(12) United States Patent
Stopek

(10) Patent No.: US 8,061,520 B2
(45) Date of Patent: Nov. 22, 2011

(54) MEDICAL DEVICE PACKAGE INCLUDING SELF-PUNCTURABLE PORT

(75) Inventor: Joshua B. Stopek, Yalesville, CT (US)

(73) Assignee: Tyco Healthcare Group LP, North Haven, CT (US)

( * ) Notice: Subject to any disclaimer, the term of this patent is extended or adjusted under 35 U.S.C. 154(b) by 58 days.

(21) Appl. No.: 12/442,068

(22) PCT Filed: Oct. 5, 2007

(86) PCT No.: PCT/US2007/021422
§ 371 (c)(1),
(2), (4) Date: Mar. 19, 2009

(87) PCT Pub. No.: WO2008/045339
PCT Pub. Date: Apr. 17, 2008

(65) Prior Publication Data
US 2010/0004620 A1  Jan. 7, 2010

Related U.S. Application Data

(60) Provisional application No. 60/850,063, filed on Oct. 6, 2006.

(51) Int. Cl.
*A61B 19/02* (2006.01)
*B65D 81/26* (2006.01)
*B67D 67/01* (2006.01)

(52) U.S. Cl. .......... 206/438; 206/207; 222/83; 604/408; 604/411

(58) Field of Classification Search .............. 206/207, 206/210, 363–370, 380, 438–439; 604/408, 604/411–413, 415; 222/80–83.5, 541.9
See application file for complete search history.

(56) References Cited

U.S. PATENT DOCUMENTS

| | | | |
|---|---|---|---|
| 2,764,979 A | 10/1956 | Henderson | |
| 3,545,608 A | 12/1970 | Berger et al. | |
| 3,648,949 A | 3/1972 | Berger et al. | |
| 3,905,375 A | 9/1975 | Toyama | |
| 4,018,222 A | 4/1977 | Mcaleer et al. | |
| 4,113,090 A | 9/1978 | Carstens | |
| 4,259,184 A | 3/1981 | D'Arnal | |
| 4,366,901 A | 1/1983 | Short | |
| 4,387,727 A | 6/1983 | Sandstrom | |
| 4,424,898 A | 1/1984 | Thyen et al. | |
| 4,601,704 A * | 7/1986 | Larkin | 604/416 |
| 4,699,271 A | 10/1987 | Lincoln et al. | |
| 4,896,767 A | 1/1990 | Pinheiro | |
| 4,961,498 A | 10/1990 | Kalinski et al. | |
| 4,967,902 A | 11/1990 | Sobel et al. | |
| 5,024,322 A | 6/1991 | Holzwarth | |

(Continued)

FOREIGN PATENT DOCUMENTS

DE  43 23 666  1/1994

(Continued)

OTHER PUBLICATIONS

International Search Report for PCT/US07/021422 date of completion is May 18, 2008 (3 pages).

(Continued)

*Primary Examiner* — Bryon Gehman

(57) ABSTRACT

The present disclosure provides a medical device package including a container for receiving a medical device and a self-puncturabie port.

5 Claims, 2 Drawing Sheets

U.S. PATENT DOCUMENTS

| | | | |
|---|---|---|---|
| 5,052,551 A | 10/1991 | Cerwin et al. | |
| 5,056,658 A | 10/1991 | Sobel et al. | |
| 5,099,994 A | 3/1992 | Kalinski et al. | |
| 5,131,533 A | 7/1992 | Alpern | |
| 5,131,553 A | 7/1992 | Geasland | |
| 5,165,217 A | 11/1992 | Sobel et al. | |
| 5,179,818 A | 1/1993 | Kalinski et al. | |
| 5,180,053 A | 1/1993 | Cascio et al. | |
| 5,192,483 A | 3/1993 | Kilgrow et al. | |
| 5,213,210 A | 5/1993 | Cascio et al. | |
| 5,222,978 A | 6/1993 | Kaplan et al. | |
| 5,228,565 A | 7/1993 | Sinn | |
| 5,230,424 A | 7/1993 | Alpern et al. | |
| 5,236,083 A | 8/1993 | Sobel et al. | |
| 5,246,104 A | 9/1993 | Brown et al. | |
| 5,249,671 A | 10/1993 | Sinn | |
| 5,249,673 A | 10/1993 | Sinn | |
| 5,263,585 A | 11/1993 | Lawhon et al. | |
| 5,271,495 A | 12/1993 | Alpern | |
| 5,284,240 A | 2/1994 | Alpern et al. | |
| 5,334,180 A * | 8/1994 | Adolf et al. | 604/411 |
| 5,350,060 A | 9/1994 | Alpern et al. | |
| 5,359,831 A | 11/1994 | Brown et al. | |
| 5,366,081 A | 11/1994 | Kaplan et al. | |
| 5,392,918 A | 2/1995 | Harrison | |
| 5,407,071 A | 4/1995 | Lawhon et al. | |
| 5,417,036 A | 5/1995 | Brown et al. | |
| 5,433,315 A | 7/1995 | Brandau | |
| 5,447,966 A | 9/1995 | Hermes et al. | |
| 5,462,162 A | 10/1995 | Kaplan et al. | |
| 5,468,252 A | 11/1995 | Kaplan et al. | |
| 5,472,081 A | 12/1995 | Kilgrow et al. | |
| 5,503,266 A | 4/1996 | Kalbfeld et al. | |
| 5,575,382 A | 11/1996 | Sobel et al. | |
| 5,628,395 A | 5/1997 | Daniele et al. | |
| 5,655,652 A | 8/1997 | Sobel et al. | |
| 5,669,490 A | 9/1997 | Colligan et al. | |
| 5,675,961 A | 10/1997 | Cerwin et al. | |
| 5,681,740 A | 10/1997 | Messier et al. | |
| 5,704,469 A | 1/1998 | Daniele et al. | |
| 5,733,293 A | 3/1998 | Scirica et al. | |
| 5,788,062 A | 8/1998 | Cerwin et al. | |
| 5,887,706 A | 3/1999 | Pohle et al. | |
| 5,906,273 A | 5/1999 | Pohle et al. | |
| 5,918,733 A | 7/1999 | Cerwin et al. | |
| 5,960,956 A | 10/1999 | Langanki et al. | |
| 6,016,905 A | 1/2000 | Gema et al. | |
| 6,047,815 A | 4/2000 | Cerwin et al. | |
| 6,076,659 A | 6/2000 | Baumgartner et al. | |
| 6,096,532 A | 8/2000 | Armstrong et al. | |
| 6,098,796 A | 8/2000 | Januzeli et al. | |
| 6,105,339 A | 8/2000 | Pohle et al. | |
| 6,135,272 A | 10/2000 | Sobel et al. | |
| 6,135,385 A | 10/2000 | Martinez de Lahidalga | |
| 6,138,440 A | 10/2000 | Gemma | |
| 6,260,699 B1 | 7/2001 | Kaplan et al. | |
| 6,306,424 B1 | 10/2001 | Vyakarnam et al. | |
| 6,333,029 B1 | 12/2001 | Vyakarnam et al. | |
| 6,365,149 B2 | 4/2002 | Vyakarnam et al. | |
| 6,394,269 B1 | 5/2002 | Rudnick et al. | |
| 6,398,031 B1 | 6/2002 | Frezza | |
| 6,415,939 B1 * | 7/2002 | Redmond | 220/375 |
| 6,423,252 B1 | 7/2002 | Chun et al. | |
| 6,464,071 B2 | 10/2002 | Baumgartner | |
| 6,481,568 B1 | 11/2002 | Cerwin et al. | |
| 6,481,569 B1 | 11/2002 | Alpern | |
| 6,533,112 B2 | 3/2003 | Warnecke | |
| 6,534,084 B1 | 3/2003 | Vyakarnam et al. | |
| 6,644,469 B2 | 11/2003 | Alpern | |
| 6,648,133 B1 | 11/2003 | Blaschke et al. | |
| 6,659,994 B1 | 12/2003 | Mader et al. | |
| 6,685,058 B2 * | 2/2004 | Redmond | 222/541.9 |
| 6,692,738 B2 | 2/2004 | MacLaughlin et al. | |
| 6,807,737 B1 | 10/2004 | Davia | |
| 6,986,735 B2 | 1/2006 | Abraham et al. | |
| 7,056,503 B2 | 6/2006 | Rees et al. | |
| 7,078,032 B2 | 7/2006 | MacLaughlin et al. | |
| 7,112,417 B2 | 9/2006 | Vyakarnam et al. | |
| 7,121,999 B2 | 10/2006 | Abraham et al. | |
| 7,129,035 B2 | 10/2006 | Goldstein et al. | |
| 7,401,703 B2 | 7/2008 | McMichael et al. | |
| 7,435,423 B2 * | 10/2008 | Collinge et al. | 424/400 |
| 2002/0156471 A1 | 10/2002 | Stern et al. | |
| 2003/0198666 A1 | 10/2003 | Abbas et al. | |
| 2004/0131956 A1 | 7/2004 | Machiguchi et al. | |
| 2004/0153125 A1 | 8/2004 | Roby | |
| 2005/0079200 A1 | 4/2005 | Rathenow et al. | |
| 2005/0167309 A1 | 8/2005 | Iwatschenko | |
| 2005/0220770 A1 | 10/2005 | Scott et al. | |
| 2005/0278012 A1 | 12/2005 | Vonderwalde | |
| 2006/0027467 A1 | 2/2006 | Ferguson | |
| 2006/0029722 A1 | 2/2006 | Larson et al. | |
| 2006/0163752 A1 | 7/2006 | Wang et al. | |
| 2006/0193884 A1 | 8/2006 | Stopek et al. | |
| 2007/0170080 A1 | 7/2007 | Stopek et al. | |

FOREIGN PATENT DOCUMENTS

| | | |
|---|---|---|
| EP | 0 418 059 | 3/1991 |
| EP | 0 558 085 | 9/1993 |
| EP | 0 558 086 | 9/1993 |
| EP | 0 564 274 | 10/1993 |
| EP | 0 726 062 | 8/1996 |
| EP | 0 728 445 | 8/1996 |
| EP | 1 275 343 | 1/2003 |
| EP | 1 312 556 | 5/2003 |
| EP | 1 316 291 | 6/2003 |
| GB | 1 327 865 | 8/1973 |
| JP | 10306228 | 11/1998 |
| WO | WO 98/11932 | 3/1998 |
| WO | WO 99/37233 | 7/1999 |
| WO | WO 01/36289 | 5/2001 |
| WO | WO 03/008285 | 1/2003 |
| WO | WO 03/092779 | 11/2003 |
| WO | WO 03/101334 | 12/2003 |
| WO | WO 2006/126926 | 11/2006 |
| WO | WO 2007/104107 | 9/2007 |
| WO | WO 2008/045339 | 4/2008 |

OTHER PUBLICATIONS

European Search Report for EP 07001216.6-1265 date of completion is May 22, 2007.

European Search Report for EP 07253902.6-1526 date of completion is Jan. 22, 2008.

European Search Report for EP 08253979.2-2310 date of completion is Apr. 21, 2009.

International Search Report for PCT/US07/004478 date of completion is Nov. 20, 2007 (10 pages).

International Search Report for PCT/US2007/021421 date of completion is Feb. 26, 2008 (10 pages).

International Search Report for PCT/US2008/002457 date of completion is Jun. 6, 2008.

International Search Report for PCT/US2008/002458 date of completion is Jun. 10, 2008.

* cited by examiner

MEDICAL DEVICE PACKAGE INCLUDING SELF-PUNCTURABLE PORT

CROSS-REFERENCE TO RELATED APPLICATION

This application is a National State Application of PCT/US2007/021422 filed Oct. 5, 2007 under 35USC §371 (a), which claims priority of U.S. Provisional Patent Application Ser. No. 60/850,063 filed Oct. 6, 2006, the disclosures of each of the above-identified applications are hereby incorporated by reference in their entirety.

BACKGROUND

1. Technical Field

The present disclosure relates generally to packaging for medical devices, and more particularly, to a package including a container having an area configured and dimensioned for receiving a medical device and a self-puncturable port including an integral puncturing structure, for permitting the passage of at least one agent between the outside of the container and the area configured and dimensioned for receiving the medical device.

2. Background of Related Art

Combination medical devices, i.e., medical devices coated with drugs or other bioactive agents, have become more prevalent commercially in recent years. There are many of these combination medical devices presently available however medical professionals are limited to using these devices in the specific combinations, dosages and strengths produced, without flexibility to after the product as needed for their respective patients. As a result, medical professionals have been known to independently combine a selected medical device with one of the many agents presently available. Since this practice is normally conducted immediately prior to use of the medical device, the medical professional is required to handle the medical device outside of the packaging, while simultaneously attempting to apply the agent using a syringe or other sharps device.

This activity not only increases the possibility of contamination of the medical device prior to coming in contact with the patient, but also increases the likelihood of a medical professional becoming injured by the sharp device while attempting to combine the agent with the device.

It would be desirable to provide a package configured for receiving a medical device, having a safe, self-puncturable port for permitting the passage of an agent between the outside of the package and the medical device contained therein, without exposing the medical professional to the possibility of a needle stick and yet minimize the likelihood of contaminating the medical device.

SUMMARY

Accordingly, a package for a medical device in accordance with the present disclosure includes a container having an area configured and dimensioned for receiving a medical device and a self-puncturable port including an integral puncturing structure for permitting the passage of at least one agent between the outside of the container and the medical device contained therein. In embodiments, the puncturing structure is positioned within the port. In embodiments, puncturing structure is positioned along the exterior of the port. The package may further include a medical device.

In other embodiments, the package includes a container having an area configured and dimensioned for receiving a medical device and a port including an integral puncturing structure, wherein the puncturing structure is movably attached to the exterior of the port. The puncturing structure is designed to be movable to penetrate or puncture the barrier between the port and the container to allow the passage of at least one agent. It is envisioned that the puncturing structure may also be detachable from the port.

BRIEF DESCRIPTION OF THE DRAWINGS

Various embodiments are described herein with reference to the drawings wherein.

DETAILED DESCRIPTION

Figure 1C:
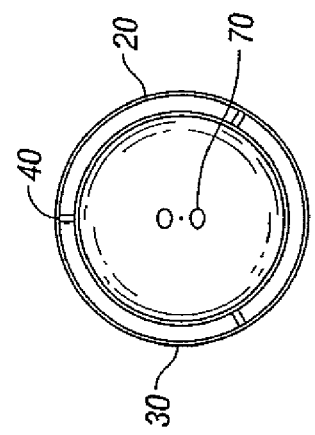
FIG. 1C is a side view of a port positioned on a container for a medical device.

The medical device packages described herein include a container for a medical device which has an area configured and dimensioned for receiving a medical device and a self-puncturable port including a puncturing structure for permitting the passage of at least one agent between the outside of the container and the area configured and dimensioned for receiving a medical device. It is envisioned that any medical device may be stored within the package. Some examples include, but are not Limited to, sutures, staples, clips, adhesives, sealants, stents, grafts, meshes, sternum closures, pins, screws, tacks, and adhesion barriers.

The container is dimensioned and configured to receive a medical device. The container may be any conventional enclosure for storing medical devices and more than one container may be combined to form the medical device packages described herein. Some examples of useful containers include, but are not limited too, pouches, paper retainers, plastic retainers, bags, trays, envelopes, Tyvek® bags, foil-packs, and the like. It is envisioned that the containers may be sealable, non-sealable, breathable, non-breathable, peelable, resealable, and combinations thereof.

The container may be manufactured from any material known to those skilled in the art which is suitable for receiving or storing a medical device. Some examples of suitable materials include, but are not limited to, polycarbonate, high-density polyethylene, polyethylene, polypropylene, thermoplastic resins, polytetrafluoroethylene, $\epsilon$-caprolactone, glycolide, l-lactide, d,l-lactide, d-lactide, meso-lactide, trimethylene carbonate, 4,4-dimethyl-1,3-dioxan-2-one, p-dioxanone, dioxepanone, $\delta$-vaterolactone, $\beta$-butyrolactone, $\epsilon$-decalactone, 2,5-diketomorpholine, pivalolactone, $\alpha,\alpha$-diethylpropiolactone, 6,8-dioxabicyclooctan-7-one, ethylene carbonate, ethylene oxalate, 3-methyl-1,4-dioxane-2,5-dione, 3,3-dimethyl-1,4-dioxane-2,5-dione, polyolefins, polysiloxanes, polyalkylene glycols, polyacrylates, aminoalkyl acrylates, polyvinylalcohols, polyvinylpyrrolidones, polyoxyethylenes, polyacrylamides, poly(2-hydroxy-ethylmethacrylate), polymethacrylamide, dextran, alginic acid, sodium alginate, polysaccharides, gelatin, cellulose, and copolymers, homopolymers, and block copolymers thereof.

The at least one agent may be selected from any bioactive and/or non-bioactive agent suitable for combination with the medical device. Suitable agents include, but are not limited to, drugs, such as antiseptics, anesthetics, muscle relaxants, antihistamines, decongestants, antimicrobial agents, anti-viral agents, anti-fungal agents, antimalarials, amebicides, antituberculosal agents, antiretroviral agents, leprostatics, antiprotazoals, antihelmitics, antibacterial agents, steroids, hematopoictic agents, antiplatelet agents, anticoagulants, coagulants, thrombolytic agents, hemorrheologic agents, hemostatics, plasma expanders, hormones, sex hormones, uterine-active agents, bisphosphonates, antidiabetic agents, glucose-elevating agents, growth hormones, thyroid hormones, inotropic agents, antiarrhythmic agents, calcium channel blockers, vasodilators, sympatholytics, antihyperlipidemic agents, vasopressors, angiotensin antagonists, sclerosing agents, anti-impotence agents, urinary alkanizers, urinary acidifiers, anticholinergics, diuretics, bronchodilators, surfactants, antidepressants, antipsychotics, antianxiety agents, sedatives, hypnotics, barbiturates, antiemetic agents, analgesics, stimulants, anticonvulsants, antiparkinson agents, proton pump inhibitors, $H_2$-antagonists, antispasmodics, laxatives, antidiarrheals, antiflatulents, digestive enzymes, gallstone solubilizing agents, antihypertensive agents, cholesterol-lowering agents, radiopaque agents, immune globulins, monoclonal antibodies, antibodies, antitoxins, antivenins, immunologic agents, anti-inflammatory agents, antineoplastic agents, alkylating agents, antimetabolites, antimitotic agents, radiopharmaceuticals, vitamins, herbs, trace elements, amino acids, enzymes, chelating agents, immunomodulatory agents and immunosuppressive agents; coating materials such as lubricants, and non-bioabsorbable substances such as silicone, beeswax, or polytetrafluoroethylene, as well as absorbable substances such as collagen, chitosan, chitin, carboxymethylcellulose, and homopolymers and/or copolymers of polyalkylene glycols, and higher fatty acids or salts or esters thereof, glycolic acid, a glycolide, lactic acid, a lactide, p-dioxanone, valerolactone and other lactones derived from linear aliphatic hydroxycarboxylic acids, α-hydroxybutyric acid, ethylene carbonate, ethylene oxide, propylene oxide, propylene carbonate, malic acid ester lactones, succinic acid, adipic acid and other linear aliphatic dicarboxytic acids, and linear aliphatic diols such as butanediol and hexanediol; diluents, such as water, saline, dextrose in water and lactated ringers; wound healing agents; adhesives; sealants; blood products; blood components; preservatives; colorants; dyes; ultraviolet absorbers; ultraviolet stabilizers; photochromic agents; anti-adhesives; proteins; polysaccharides; peptides; genetic material; viral vectors; nucleic acids; nucleotides; plasmids; lymphokines; radioactive agents; metals; alloys; salts; growth factors; growth factor antagonists; cells; hydrophobic agents; hydrophilic agents; immunological agents; anti-colonization agents; diagnostic agents; imaging agents; and combinations thereof.

In addition to the container and the area configured and dimensioned for receiving a medical device, the package includes a self-puncturable port. The self-puncturable port permits the passage of at least one agent between the outside of the container and the area configured and dimensioned for receiving a medical device without the need of a separate needle or sharps device. The port includes puncture-capable part, i.e., a puncturing structure, affixed to the port. The puncturing structure is capable of penetrating or puncturing the barrier located between the container and the port.

Figure 1B:
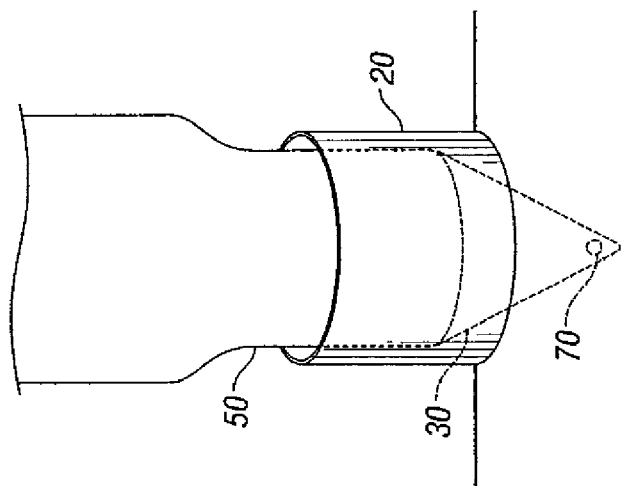
FIG. 1B is a top view of a port positioned on a container for a medical device.
Figure 1A:
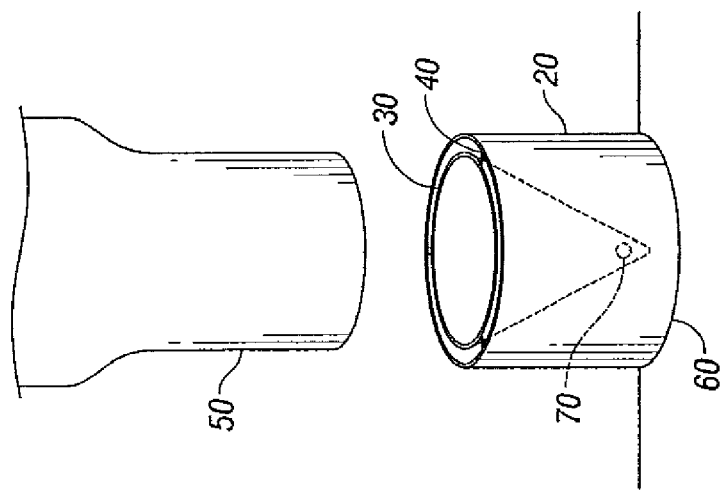
FIG. 1A is a side view of a port positioned on a container for a medical device.

Turning now to FIGS. 1A-1C, self-puncturable port 20 is shown containing puncturing structure 30 therein. In some embodiments, puncturing structure 30 is attached to port 20 via tabs 40. Delivery device 50 does not include a needle or sharpened end and is designed to matingly engage port 20.

Upon engagement, delivery device 50 is forced into port 20 thereby weakening tabs 40 and releasing puncturing structure 30 from port 20. Puncturing structure 30 is forced deeper in port 20 by delivery device 50 to puncture barrier 60 located below port 20. Puncturing structure 30 includes at least one opening 70 which is designed to allow the passage of the agent between the outside of the container and the area configured and dimensioned to receive the medical device following the puncturing of barrier 60.

Figure 2A:
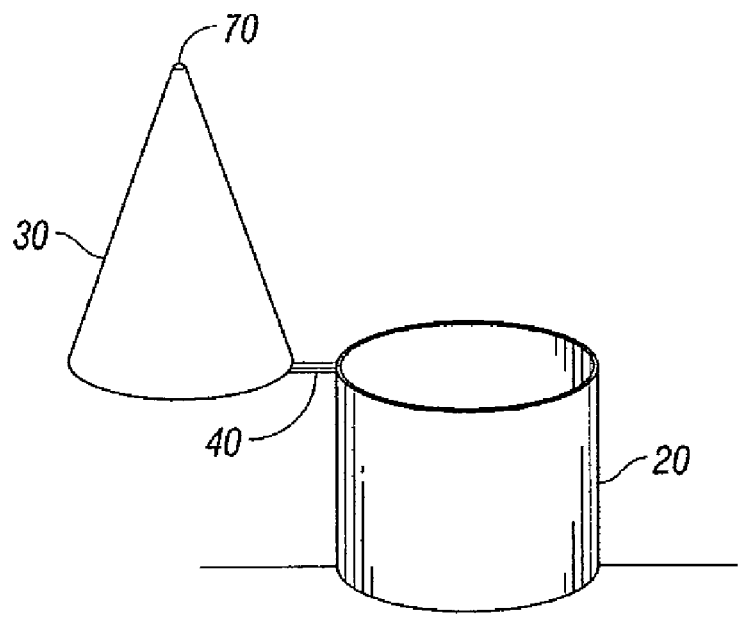
FIG. 2A is a side view of a port positioned on a container for a medical device.
Figure 2B:
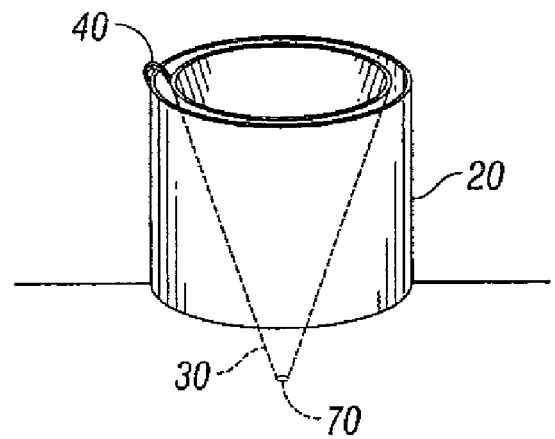
FIG. 2B is a side view of a port positioned on a container for a medical device.

In other embodiments, puncturing structure 30 is movably attached to port 20, a shown in FIGS. 2A and 2B. In these embodiments, puncturing structure 30 is capable of being manipulated by a device or the hand of the medical personnel to pivot about tab 40 to enter and penetrate port 20 to a sufficient depth to puncture barrier 60.

In still other embodiments, puncturing structure 30 may be removable from port 20. It is envisioned that the puncturing structure may be detached from port and positioned onto the delivery device. The delivery device with the puncturing structure may then engage the port and puncture the barrier located below.

The puncturing structure may be made from any material suitable for puncturing the barrier of the container. Some examples include but are not limited to polymeric and metallic compositions. In addition the puncturing structure may be configured and dimensioned into any shape suitable for puncturing the barrier. As shown in FIG. 2, a puncturing structure having a conical shape is particularly useful.

The port may be positioned along any side, edge or corner of the container. In embodiments wherein the package includes more than one container, the port may be positioned along any side, edge or corner of any of the containers included in the package. In addition, the package may contain more than one port and/or more than container may share a common port. In some embodiments, the port may be designed in such a way that only a particular injector can mate with the port, i.e., male/female, threaded or lock/key type hubs. In some embodiments, the port may include a piercable barrier positioned between the outside of the container and the area configured for receiving the medical device.

It is well understood that various modifications may be made to the embodiments disclosed herein. Therefore, the above description should not be construed as limiting, but merely as exemplifications of particularly useful embodiments. Those skilled in the art will envision other modifications within the scope and spirit of the claims appended hereto.

The invention claimed is:

1. A package comprising:
a medical device;
a container having an area configured and dimensioned for receiving the medical device; and,
a self-puncturable port including a puncturing structure, the puncturing structure containing at least one opening for permitting the passage of at least one agent through the at least one opening of the puncturing structure and between the outside of the container and the area of the container for receiving the medical device, wherein the puncturing structure is positioned on the outside of the package and movably attached to an exterior of the port by at least one tab.

2. The package of claim 1 wherein the medical device is selected from the group consisting of sutures, staples, clips, grafts, stents, meshes, sternum closures, pins, screws, tacks, and combinations thereof.

3. The package of claim 1 wherein the medical device is a suture.

4. The package of claim 1 wherein the at least one agent is selected from the group consisting of drugs, coating materials, diluents, wound healing agents, adhesives, sealants, blood products, blood components, preservatives, colorants dyes, ultraviolet absorbers, ultraviolet stabilizers, photochromic agents, anti-adhesives, proteins, polysaccharides, peptides, genetic material, viral vectors, nucleic acids, nucleotides, plasmids, lymphokines, radioactive agents, metals, alloys, salts, growth factors, growth factor antagonists, cells, hydrophobic agents, hydrophilic agents, immunological agents, anti-colonization agents, diagnostic agents, imaging agents, and combinations thereof.

5. The package of claim 1 wherein the at least one agent is a diluent.

* * * * *